US012576186B1

(12) United States Patent
Delk et al.

(10) Patent No.: US 12,576,186 B1
(45) Date of Patent: Mar. 17, 2026

(54) COLLAGEN PELLET AND METHODS FOR MAKING AND USE

(71) Applicants: Robert E. Delk, Dallas, TX (US);
Bernardo S. Vielma, Garland, TX (US)

(72) Inventors: Robert E. Delk, Dallas, TX (US);
Bernardo S. Vielma, Garland, TX (US)

( * ) Notice: Subject to any disclaimer, the term of this patent is extended or adjusted under 35 U.S.C. 154(b) by 1435 days.

(21) Appl. No.: 16/974,188

(22) Filed: Nov. 6, 2020

Related U.S. Application Data

(60) Provisional application No. 62/974,088, filed on Nov. 13, 2019.

(51) Int. Cl.
| | |
|---|---|
| *A61L 27/24* | (2006.01) |
| *A61M 37/00* | (2006.01) |
| *B29C 48/00* | (2019.01) |
| *B29C 48/08* | (2019.01) |

(52) U.S. Cl.
CPC ......... *A61L 27/24* (2013.01); *A61M 37/0069* (2013.01); *B29C 48/0022* (2019.02); *B29C 48/08* (2019.02); *B29K 2089/00* (2013.01)

(58) Field of Classification Search
None
See application file for complete search history.

(56) References Cited

U.S. PATENT DOCUMENTS

| | | | | |
|---|---|---|---|---|
| 5,281,197 A | * | 1/1994 | Arias ................ | A61M 37/0069 604/209 |
| 2008/0287913 A1 | * | 11/2008 | Schwab ............ | A61M 37/0069 604/60 |
| 2010/0324529 A1 | * | 12/2010 | Bachman .......... | A61M 37/0069 604/506 |
| 2016/0296739 A1 | * | 10/2016 | Cleveland ......... | A61M 5/31526 |

* cited by examiner

*Primary Examiner* — Manuel A Mendez
(74) *Attorney, Agent, or Firm* — Robert E. Wise

(57) ABSTRACT

A mass or pellet of collagen, such as Type 1 bovine collagen, can advantageously be implanted last into a subcutaneous incision into which one or more medicinal and/or pharmaceutical masses or pellets have already been disposed in the subcutaneous channel incised into the tissue under the skin. The collagen is preferably shaped in the form of a pellet similar in size and shape to the medicinal and/or pharmaceutical element that is to be implanted in a patient, but other shapes and sizes of collagen can be selected for implantation. A pellet of implantable collagen can be made by rolling out the collagen into a cylinder shape, lyophilizing the collagen, then physically cross-linking the collagen by heating, and using forming tools to form the collagen into a desired shape and size. Before being formed, the collagen (which is normally a dry fine powder) may be combined with a binder component, so that the collagen pellet has sufficient mechanical solidity for a sufficient time to be implanted. One preferred method of making a collagen pellet is to hand-roll a collagen sheet or extrude the collagen into an elongated cylinder shape, and to then lyophilize (freeze dry) the collagen cylinder. Then the collagen cylinder is physically cross-linked by heating it over a period of time. The collagen cylinder can then be cut into pellets of the desired length. A method of implanting a collagen pellet is disclosed.

2 Claims, 3 Drawing Sheets

COLLAGEN PELLET AND METHODS FOR MAKING AND USE

CROSS REFERENCE TO RELATED APPLICATIONS

The present application claims the benefit of 35 U.S.C. § 111(b) U.S. Provisional Application Ser. No. 62/974,088, filed Nov. 13, 2019, entitled "Collagen Pellet".

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

This invention relates to the field of implantable collagen elements, the manner of making the collagen element, and the method of implanting the collagen element in conjunction with a medicinal and/or pharmaceutical implanted element.

2. Description of Related Art Including Information Under 37 CFR 1.97 and 1.98

It is common for various medicinal or pharmaceutical drugs to be implanted subcutaneously in the tissue under the skin of a human or animal patient. For example, pellets containing a hormone, such as testosterone, estrogen, and/or progesterone, can be implanted into the patient (an animal or person) using a standard trocar. Implanting the pellet with the trocar leaves a relatively deep but narrow incision in the skin. This incision can lead to scarring. The incision can also become infected, which may complicate healing and cause even more scarring than normal. Further, the incision wound may produce exudates that can inhibit or slow healing, and cause the medicinal and/or pharmaceutical pellets to extrude from the wound.

Collagen is known to assist in wound treatment. Collagen has a relatively low pH which minimizes infection and promotes rapid healing. However, collagen is generally in the form of a fine dry powder which will not hold a firm shape when one attempts to mechanically press it into pellet form.

BRIEF SUMMARY OF THE INVENTION

The applicants have discovered that a small mass or pellet of collagen can advantageously be implanted last into a subcutaneous incision into which one or more medicinal and/or pharmaceutical masses or pellets (such as, but not limited to, hormone pellets, testosterone pellets, estrogen pellets, progesterone pellets, and the like) have already been disposed under the skin. The applicants have discovered that implanting the collagen pellet or mass lastly over the medicinal and/or pharmaceutical pellet(s) or mass(es) has advantageous and desirable effects, such as minimizing infection of the incision wound during healing, the promotion of rapid healing, and/or the minimization of scarring caused by the incision wound. The invention also prevents the lower medicinal and/or pharmaceutical pellet(s) from extruding from the implantation hole or channel.

Any type of collagen that accomplishes some or all of the purposes and advantages specified in this application can be used as recited in this application. However, the applicants preferably use Type 1 bovine collagen in practicing this invention. Persons of ordinary skill in this art who read and understand this application disclosure will be able to ascertain and use various types of collagen other than Type 1 bovine collagen that are also suitable for practicing this invention.

DETAILED DESCRIPTION OF THE INVENTION

Figure 1:
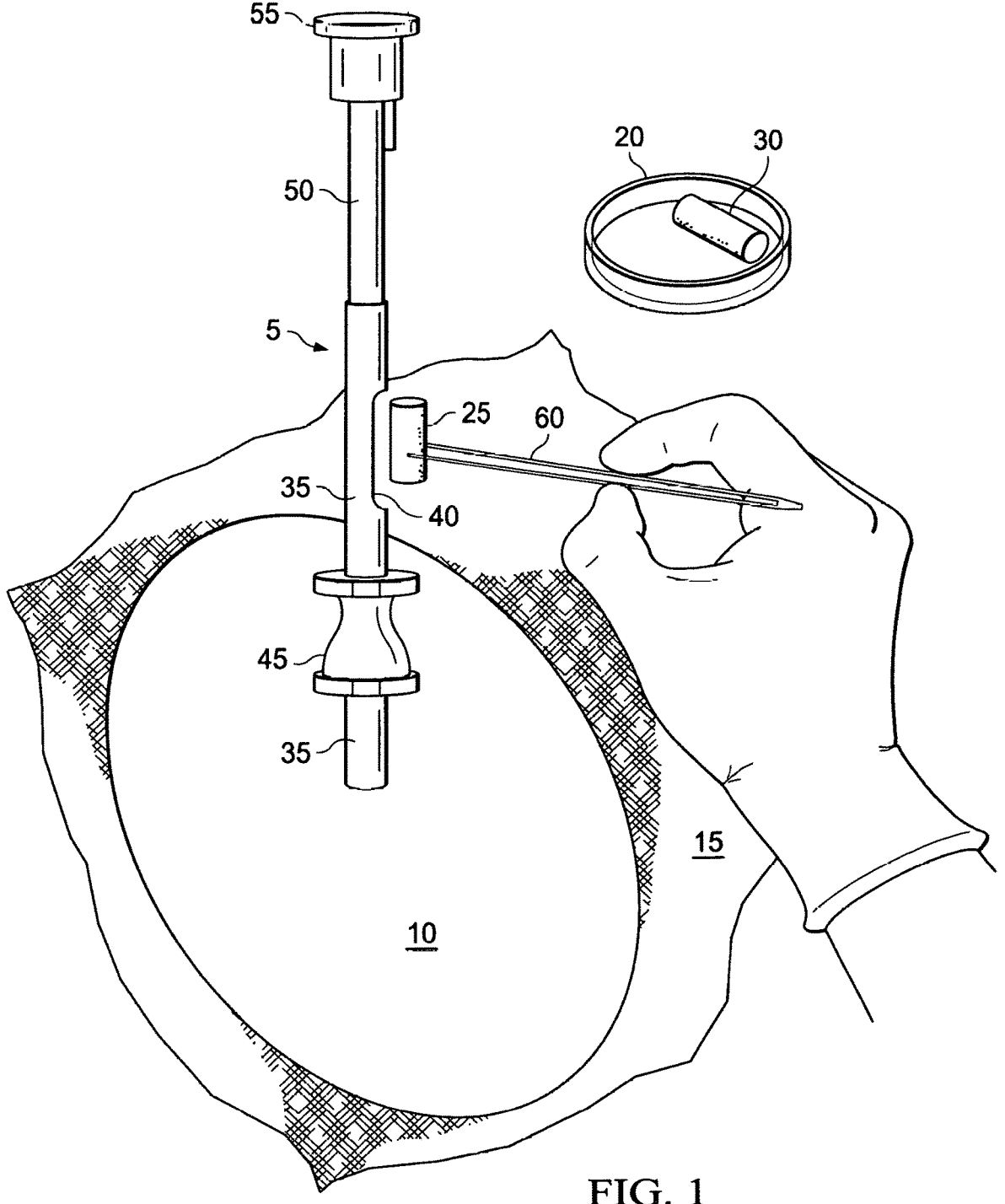
FIG. 1 shows the insertion of a trocar into a patient and the placement of a pellet comprising a medicinal and/or pharmaceutical property into the loading port of the trocar's cannula.

This invention can be practiced with a wide range of collagen masses of differing sizes and shapes. The significant factor is that at least one collagen mass or pellet be disposed within the incision hole or channel in a manner such that it is nearer the surface of the skin than any of the medicinal and/or pharmaceutical elements that were placed in the incision hole or channel.

Collagen pellets made according to the invention disclosed in this application may be supplied to physicians or other practitioners in vials containing one, two, three, or more collagen pellets in the vial. Physicians may choose to implant one or more than one collagen pellet in a particular implantation procedure. For example, a physician may first implant one or more than one collagen pellets subcutaneously into one implantation hole or channel, followed by the implantation of one or more than one pellet having one or more medicinal and/or pharmaceutical properties. Following that, the physician may then implant one or more collagen pellets in the implantation hole or channel. This will then result in the medicinal and/or pharmaceutical pellet(s) (for example, a hormone pellet) being disposed in the implantation hole with one or more collagen pellets disposed deeper (or further from the skin surface) in the patient's tissue than the medicinal and/or pharmaceutical pellet(s) and also one or more collagen pellets disposed above (or closer to the skin surface) than the medicinal and/or pharmaceutical pellet(s). This invention, at a minimum, would comprise the implantation of one collagen pellet above (or closer to the skin surface) than the one or more medicinal and/or pharmaceutical pellet(s), but this invention also encompasses the implantation of one or more collagen pellets below the medicinal and/or pharmaceutical pellet(s), and it encompasses the implantation of plural collagen pellets above the medicinal and/or pharmaceutical pellet(s). Each individual physician or practitioner will, in the exercise of his or her own professional expertise after reading this invention disclosure, make a decision as to how many collagen pellets to insert and where in the implantation channel to insert them.

Cylindrical Pellet

The applicants have found that one preferable shape for the collagen mass is that of an elongated cylindrical pellet. The cylindrical pellet can preferably have a cylinder diameter that has a relatively uniform diameter, with the diameter of the cylinder being approximately equal to the diameter of the hole incised through the skin and into the tissue of the patient to enable implantation of the element(s) comprising medicinal and/or pharmaceutical properties. Having a cylinder diameter approximately equal to that of the incision hole or channel enables the collage pellet to be implanted relatively easy and still have the collagen pellet substantially fill the incision hole or channel so that it performs its function well. By way of example only and without limitation, a pellet may be shaped in the form of a cylindrical rod being approximately ⅛-inch in diameter and ½-inch in length. However, the exact size and shape of the pellet is a matter of design choice. Persons of ordinary skill in this art who read and understand this disclosure will be able to design pellets of various sizes and shapes to suit their individual purposes, while still using the inventive concepts disclosed in this disclosure. However, it must be understood that cylindrical pellets are only one shape of many that can be used in the practice of this invention.

Further, since the formation of the collagen pellet may tend to compress the collagen somewhat, once the collagen pellet is implanted subcutaneously in the tissue of the patient, the collagen pellet may expand somewhat within the implantation channel after being implanted. This can be advantageous in that the expansion of the collagen pellet, being disposed above (or nearer to the skin surface) the medicinal and/or pharmaceutical pellet (for example, a hormone pellet), will minimize the tendency of the medicinal and/or pharmaceutical pellet to extrude from the implantation channel as it is absorbed by the body.

Use of Trocar

One way to implant both the one or more pellet(s) having a medicinal and/or pharmaceutical property and the one or more collagen pellet(s) is by using a standard trocar or a similar instrument. By way of description and not to limit the term, a trocar is an instrument commonly used for inserting relatively solid elements through the skin of a person or animal and into the subcutaneous tissue thereof. A trocar typically is relatively long and thin. It is essentially a thin hollow cannula. The cannula will have a loading port through part of the cannula through which elements can be placed within the cannula. The cannula may have a holding device around the cannula to make it easier to grasp and manipulate by the user. The cannula is typically made of stainless steel or another suitable metal. One end of the cannula—the end that will cut through the skin of the human or animal and enter into the subcutaneous tissue-will be sharpened to enable the sharpened end of the cannula to easily penetrate the skin and tissue, and insert the cannula to the chosen depth within the tissue of the patient. At the opposite end of the cannula will be a plunger situated in the cannula above an opening into which the solid element is loaded for insertion subcutaneously. The plunger's arm will extend most of the length of the cannula to enable the plunger to push the solid element from the loading opening down through the cannula and out of the sharpened end and into the subcutaneous tissue of the person/animal. The plunger will typically have a broadened base at the far end by which the user can press down on the plunger to move the plunger within the cannula and push whatever is in front of the plunger within the cannula. In use, a physician will typically first pull the trocar's plunger up away from the sharpened end such that the barrel of the plunger is above the loading opening. The physician will insert the sharpened end of the trocar through the skin of the person/animal and down into the subcutaneous tissue to the desired depth. Then the loading opening will be loaded through the loading port with the solid element, typically a pellet or mass having a medicinal or pharmaceutical quality. The physician will then press on the plunger down, causing the plunger to push the solid element to pass down through the cannula until it exits the cannula at the sharpened end and is deposited into the tissue adjacent the end of the cannula's sharpened end. The trocar can then be withdrawn slightly to enable yet another pellet to be implanted, or the trocar can be completely withdrawn from the person or animal, leaving behind the pellet(s) or mass(es) in the tissue of the patient. While a trocar is a preferred device for practicing this invention, persons of ordinary skill in this art will be able to choose among existing instruments, or even design new instruments, that will perform the function intended and described in this disclosure, and all of these instruments would come within this invention disclosure.

It is also possible to implant pellets subcutaneously into a person or animal using devices or methods other than that of a trocar. This invention is not limited to the use of a trocar, but can be practiced using any instrument and/or method that accomplishes the purposes and teachings of this invention.

Forming the Collagen Pellet

A pellet of implantable collagen can be made to be subcutaneously implantable using a number of manufacturing methods, such as:

(1) rolling out the collagen into a cylinder shape, or forming a sheet of collagen to the desired thickness, and die-cutting the collagen into the desired size;

(2) lyophilizing collagen, then cross-linking and using forming tools to form the collagen into a desired shape and size; and/or (3) combining the collagen with a binder component, although combining the collagen with a binder component is optional but not necessary.

A combination of these methods could be used as well.

1. Die Cutting Collagen

A sheet of collagen can be formed and then die cut to a preferred strip size. The strip of collagen is then rolled (by hand or by another suitable means) into a cylinder shape or another suitable shape for subcutaneous implantation into a person or animal.

2. Lyophilizing Collagen and Physically Cross-Linking it

A solid pellet of collagen suitable for subcutaneous implantation into a person or animal can be obtained by shaping a pellet of collagen, after which the collagen pellet is lyophilized. A lyophilizer freezes the material placed in it in a high vacuum. The collagen is placed into a tool, or on a tray, that creates the shape and size of pellet that is desired and then the collagen is frozen in a high vacuum, which gives the collagen relative solidity. Following freeze-drying, the collagen pellet is ready to be cut to the desired size, rolled to the specific strength desired, and then sterilized.

One novelty of our invention is that one preferred method of making the collagen pellet is to form or extrude the collagen into a rod shape (an elongated cylinder) and to then lyophilize (freeze dry) the rod. Then the rod is physically cross-linked by heating it over a period of time. Cross-linking can be accomplished by heating the rod at a temperature of 125 degrees Centigrade for a minimum of 8 hours. Optionally, the rod may be cross-linked by heating the rod at a temperature within the range of 90 degrees Centigrade to 150 degrees Centigrade for a time selected within the range of from 8 to 24 hours. Persons of ordinary skill in this art who read this application will be able to determine other heating times and temperatures that are suitable using on the ordinary skill in this art. Then the collagen rod is dampened in a misting purified water spray. Then the moistened collagen rod is compression rolled to form it tightly to the desired cylindrical diameter. After that the elongated rod can be cut into multiple pellets of the desired length. Physically cross-linking the collagen rod has been found to enable us to use 100% pure Type 1 collagen. This is a pure collagen product with no added chemicals or contaminants. The advantage of compression rolling the collagen rod is that, when the rod is cut into pellets and when the pellets are implanted in the incision hole or channel of the body of the patient, the pellet will absorb body fluids and swell from 35% to 50% in diameter, thereby forming a blockage in the incision hole or channel and substantially preventing the medicinal and/or pharmaceutical pellets from moving upwardly toward the skin surface (which would be undesirable)

3. Use of a Binder

Collagen is normally a fine dry powder that generally will not hold a solid pellet form when mechanically compressed. To implant collagen into the subcutaneous tissue via an incision through the skin and subcutaneous tissue, it may be desirable to use a binder component, such as 5% to 30% Cholesterol or Lactose, in combination with the collagen. This can hold the collagen/binder combination together in pellet form until it is placed subcutaneously into the patient (animal or person) where it will perform its intended function.

A binder material can be combined with collagen to form a relatively solid pellet or mass of any suitable shape that can be implanted subcutaneously into a person or animal with a standard trocar or a similar instrument after the implantation of one or more pellets or masses comprising a medicinal and/or pharmaceutical substances. It should be understood that the collagen pellet or mass (possibly combined with a binder substance) need only stay relatively solid for the amount of time it takes a physician to implant it into the subcutaneous tissue of the person or animal. Once implanted where desired in the incision under the skin, it will not matter if the pellet soon loses solidarity. In fact, it is expected to do so over time.

The collagen and the binder material are first thoroughly mixed together. Then the mixture is placed into a pellet press machine which mechanically presses the mixture to a pre-determined volume at a predetermined pressure for a pre-determined period of time. The resulting pellet is removed from the press machine, sterilized, and packaged. It can then be used at a later time to be implanted into the implantation incision, possibly using the same trocar or other instrument that already implanted the pellets or masses comprising a medicinal and/or pharmaceutical substance within the patient.

Collagen Implanted Lastly

The collagen mass or pellet will be implanted into the subcutaneous tissue of the patient last after the implantation of one or more other pellet(s) or mass(es), such that the pellet(s) and/or mass(es) lie deeper within the tissue, and further below the surface of the skin, than does the collagen mass or pellet. While preferably there will be only one collagen mass or pellet implanted in a single incision hole or channel, it is possible that more than one collagen mass or pellet could be implanted.

Effect of Collagen

Once implanted lastly in the incision hole or channel created by the trocar or similar instrument, the collagen pellet will not tend to expand significantly outwardly, but will extend upwards and downwards within the implantation hole or channel incised by the trocar or similar instrument. The collagen will absorb wound exudates created by the patient's body as the body heals the wound. The body often recognizes the medicinal and/or pharmaceutical pellet(s) as foreign objects and creates exudates in response to such objects. It is desirable for the exudates created by the patient's body to be absorbed by the collagen and this helps to maximize and hasten the healing of the wound created by the incision.

The incision wound may extend somewhat deeper than the location of the medicinal and/or pharmaceutical pellet(s) implanted within the incision, so fluid and/or exudates are produced within the wound around and below those pellets may cause upward pressure to be exerted on those pellet(s) and tend to push the pellet(s) upward out of the wound. Pellet(s) "backing out" of the wound is referred to as "extrusion". The collagen pellet being inserted above (nearer the surface of the skin) the medicinal and/or pharmaceutical pellet(s) will tend to block the hole in the skin and tissue by quickly building a structural component that will resist or prevent the deeper pellets from pushing upwards toward the skin surface and out of the implantation hole or channel. The structural component built by the collagen is a triple helix structure that will help control fibrosis in the wound site. The collagen will absorb wound exudates and reduce the upward pressure on the pellets caused by the exudates and fluid generated in the wound. This helps the medicinal and/or pharmaceutical pellets to stay in their proper subcutaneous location(s).

The presence of the collagen provides a microbial barrier within the implantation wound because collagen has a relatively low pH (generally below 4.0) that retards or even prevents microbial growth. Further the implantation of the medicinal and/or pharmaceutical pellets may create scar tissue at or near the skin surface, and the presence of scar tissue may cause problems with subsequent implantations of pellets. It is also unsightly. The implanted collagen helps to reduce or eliminate scarring and minimizes this problem. Human patients naturally will want to minimize scarring that is visible on the skin, or lies just below the skin, for aesthetic reasons.

It is common for medicinal and/or pharmaceutical pellet implantations to occur three times annually at a cost of $400 to $700 per implantation. Infection in the implantation incision, and/or extrusion of the pellet from the implantation site, can occur in up to 12% of such procedures with additional cost often incurred to fight the infection, so the cost of implantation failure or infection is quite substantial. The collagen pellet and its use as described in this invention disclosure can last about 14 days within the implantation site under the skin surface. The collagen pellet implanted above the other pellets should reduce pain experienced by the patient, reduce redness around the implantation site (which is aesthetically unsightly), and reduce swelling around the implantation site by upwards of 50%. Thus, the practice of this invention provides substantial advantages to the patient (animal or human).

Method

The following is a brief description of one preferred inventive method of implanting the collagen pellet of this invention as described above, with the collagen pellet being implanted lastly after the implantation of one or more medicinal and/or pharmaceutical pellets (such as hormone pellets, testosterone pellets, estrogen pellets, progesterone pellets, and the like). It is important to understand that, while cylindrically-shaped pellets are the preferred form, it is certainly possible to use shapes other than that of a cylindrical pellet. Any size or shape that can be implanted into the subcutaneous tissue of a patient comes within the bounds of this invention. Further, while this inventive method may normally be carried out by a physician, it could also be practiced by another healthcare professional (such as a veterinarian, physician's assistant, dentist, podiatrist, registered nurse or the like), or even by a layperson. Descriptions herein referring to a physician are only by way of example and not limitation. Further, this inventive method can be practiced on a human being or on any animal, both of which are referred to as a "patient".

In the practice of this invention, the patient's surgical field (for example, a super-iliac placement) can be cleaned and disinfected with a suitable disinfectant, and the area of the intended implantation can be draped in the normal surgical manner. The physician (or other person performing the method) can administer local anesthesia to the area of the patient's body and allow some time period to pass for the anesthesia to take effect. Using an appropriately sized scalpel, the physician makes a small incision that extends just into the fatty layer subcutaneously. Then the physician may use one hand to pinch and elevate the area of the incision and, while holding a trocar with the other hand, the physician inserts the sharp end of the trocar through the incision in the skin previously made and pushes the trocar down into the patient's subcutaneous tissue to the desired depth. The trocar can be inserted into the patient generally parallel to the facial plane of the skin that the physician pinches with one hand, with the trocar extending through the fatty layer of the skin. Alternatively, the trocar may be inserted generally perpendicular to the facial plane of the skin or at some desired angle to that facial plane. Physicians will be able to determine the proper angle at which the trocar enters the patient depending on the application.

With the physician still pinching the patient's skin and the trocar inserted, the physician implants the one or more medicinal and/or pharmaceutical pellets through the trocar and into the patient. With each such pellet, the trocar's plunger can first be withdrawn past the loading port and the pellet will be picked up and inserted into the loading port of the trocar's cannula. Then the physician will push down on the plunger of the trocar, which in turn will push the pellet placed in the loading port down along the cannula until the pellet is pushed completely out of the cannula and into the proper place in the patient's subcutaneous tissue. The physician may then back the trocar out of the tissue slightly—to make sufficient room in the tissue for the next pellet—and the physician will withdraw the plunger to again open the loading port for the next pellet. The process can be repeated for the next pellet until all pellets have been properly implanted. Then, the physician can completely withdraw the trocar from the patient, affix a sterile bandage over the incision site, and the procedure is finished.

Alternatively, the physician may choose to insert all of the pellets sequentially into the trocar at one time, and insert them all simultaneously into the patient such that the collagen pellet will be the last or uppermost pellet once all pellets have been implanted. Further, the physician may choose to use another device or method besides a trocar that implants the pellets. Such alternatives would come within the scope of this invention if the collagen pellet ends up being implanted above (or nearer to the skin surface) than the pellets comprising a medicinal and/or pharmaceutical substance. This invention is not limited to the preferred method described above.

Also, this invention includes the concept of using plural collagen pellets with one or more of the plural collagen pellets implanted lastly, and the remainder of the plural collagen pellets either implanted firstly and/or interspersed among the medicinal and/or pharmaceutical pellets implanted in the patient's tissue. Further, this invention includes the concept of emplacing the medicinal and/or pharmaceutical pellets within a collagen casing and the collagen casing implanted into the patient's tissue, possibly with a separate collagen pellet disposed above the collagen casing that contains the medicinal/pharmaceutical pellets.

While the wound diameter at the skin surface is relatively small (on the order of 2 to 5 mm), it will extend substantially more deeply subcutaneously within the fatty layer of the skin, perhaps on the order of 2 to 20 cm. The collagen pellet of this invention can have an insertion diameter roughly equal to that of the hole in the skin so that, after emplacement, the collagen pellet would fill the diameter of the hole made in the patient.

It is possible, and may be desirable, to subcutaneously implant a collage pellet first, then to implant a pellet comprising a medicinal and/or pharmaceutical property subsequent to the collagen pellet, such that the medicinal and/or pharmaceutical pellet lies closer to the surface of the skin than does the collagen pellet.

In the drawing figures, FIG. 1 shows a trocar 5 that has already been inserted through the skin surface 10 of a patient (animal or human) and some distance into the subcutaneous tissue of the patient via the sharpened end of the trocar 5. Prior to insertion of the trocar 5, the physician would have sterilized the skin surface 10, draped the area around the intended incision site with sterile dressings 15, and possibly would have administered a local anesthetic to the patient. In FIG. 1, sterile dressings 15 are shown surrounding the operative field and a container 20 in which the two pellets to be implanted were placed—the single pellet 25 comprising a medicinal and/or pharmaceutical substance, and the collagen pellet 30 that will be implanted lastly. In FIG. 1, the trocar 5 is seen already inserted into the patient extending through the surface of the skin 10 at the insertion location within the operative field.

The trocar 5 comprises the hollow cannula 35, an open loading port 40 in the cannula 35 disposed relatively toward the "upper" part of the trocar (that being more distant from the sharpened "lower" end of the cannula). The trocar 5 is seen to comprise a larger manipulating handle 45 surrounding the cannula. The handle makes it easier for the physician to grasp and manipulate the trocar. The trocar also comprises a plunger which comprises a plunger rod 50 (not shown to proper scale) that has been pulled back substantially out of the cannula 35 to open the loading port 40. One end of the plunger has a wide "button" or finger rest 55 which the physician can push on to cause the plunger rod 50 to travel down the cannula 35 and push any pellets in front of it through the cannula 35 and out of the sharpened end of the cannula that lies within the subcutaneous tissue of the patient.

FIG. 1 shows the physician having already picked up from the container 20 the first pellet 25 comprising a medicinal and/or pharmaceutical substance. The physician would normally use tweezers 60 to pick up the pellet 25 and place it into the loading port 40 of the cannula 35. FIG. 1 shows the physician placing the first pellet 25 into the loading port 40 of the cannula 35 of the trocar 5, after which the physician will press down on the button 55 of the plunger rod 50, which will cause the plunger rod 50 to push the first pellet 25 all the way through the cannula 35 and out of the sharpened end 70 of the cannula 35 and into the tissue 65 of the patient. Both pellets 25 and 30 are formed in an elongated cylindrical shape with a cylinder diameter that is slightly less than that of the cannula 35 of the trocar 5, so that the pellets 25 and 30 can easily be pushed down the cannula 35 and into the subcutaneous tissue 65 of the patient.

Figure 2:
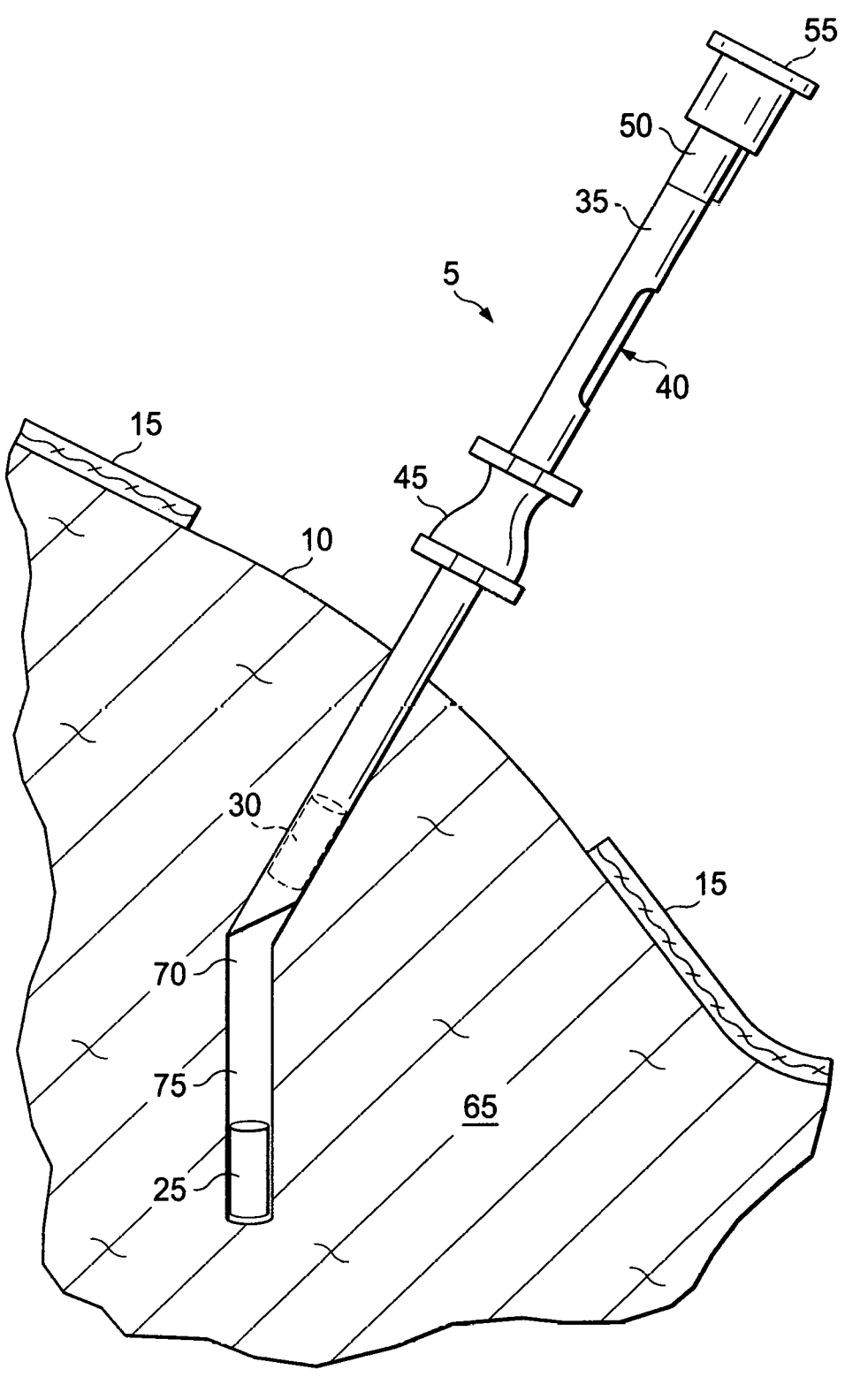
FIG. 2 shows the trocar's cannula inserted into the subcutaneous tissue of a patient, and the implantation of the first pellet within the subcutaneous tissue, that being the pellet comprising a medicinal and/or pharmaceutical property. The collagen pellet is shown being pushed down the cannula of the trocar such that it can be implanted in the patient above the first pellet.

FIG. 2 is a side view of the trocar 5 inserted via its sharpened end 70 through the surface 10 of the patient's skin and down into the subcutaneous tissue 65 of the patient, with part of the trocar 5 extending exteriorly to the skin surface 10. In FIG. 2, the physician has already loaded the first pellet 25 comprising a medicinal and/or pharmaceutical substance, and has already used the plunger rod 50 of the trocar 5 to push that first pellet 25 through the cannula 35 of the trocar 5 and into the subcutaneous tissue 65 of the patient via the sharpened end 70 of the cannula 35. The physician then withdrew the trocar 5 slightly to make a place for the second pellet 30, that being the pellet comprising collagen. The physician withdrew the plunger rod 50 sufficiently to open the loading port 40. The physician then grasped the collagen pellet 30, here called the second pellet 30, and inserted the second pellet 30 into the loading port 40 of the cannula 35 of the trocar 5, after which the physician pressed down on the button 55 of the plunger, causing the plunger rod 50 to push the second pellet 30 all the way down the cannula 35 to the sharpened end 70 of the cannula where it appears in FIG. 2. The physician will continue pushing on the plunger rod 50 of the trocar 5 until the second pellet 30 has completely left the cannula 35 and been implanted in the incision hole 75 or channel above the first pellet 25. Then the physician will withdraw the trocar 5 from the patient, leaving the two pellets 25 and 30 within the incision hole 75 or channel. Over time, the incision hole 75 or channel above the two pellets 25 and 30 will tend to close up and heal. The medicinal and/or pharmaceutical substance of the first pellet 25 will dissolve into the surrounding tissue 65 of the patient. Simultaneously, the collagen pellet 30, here called the second pellet, that is disposed above the first pellet 25 will also dissolve and operate as intended and described above.

Figure 3:
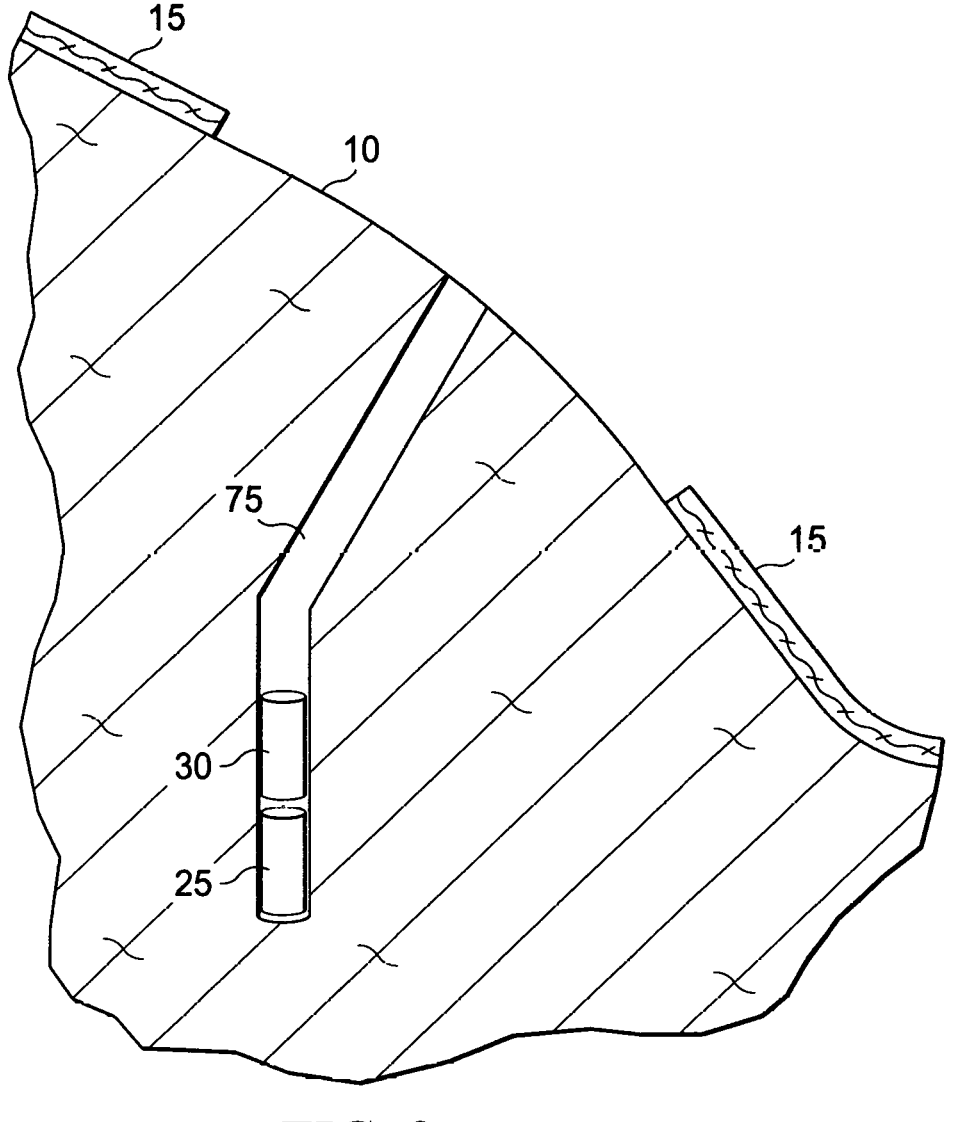
FIG. 3 shows the implantation wound in the patient's body in which the first and second pellets have been implanted sequentially in the implantation wound and the trocar withdrawn.

FIG. 3 shows the same view as in FIG. 2 except that both of the pellets 25 and 30 have now been implanted properly in the incision hole 75 or channel and the trocar 5 has been withdrawn from the patient. The physician will usually affix a sterile bandage to the wound site on the skin after withdrawing the trocar 5. FIG. 3 shows the relative dispositions of the two pellets 25 and 30, with the collagen pellet 30 disposed "above" the first pellet 25 within the incision wound 75, that being nearer to the surface of the skin 10 within the patient's tissue 65 than the first pellet 25. This relative placement is an important novel discovery of this invention.

The foregoing disclosure describes only some possible embodiments of this invention. Persons of ordinary skill in this art who read this disclosure will be able to conceive additional embodiments that come within the scope of this invention using only ordinary skill in this art. This invention is intended to be limited only by the following claims.

We claim:

1. A method of minimizing scarring and infection in the subcutaneous implantation of at least one collagen pellet having a medicinal and pharmaceutical substance into a living being, the method comprising the steps of:

1) creating an incision subcutaneously into the body of the living being;

2) inserting into the incision at least one substance that is medicinal and/or pharmaceutical for the living being; and 3) then subsequently inserting into the incision at least one predetermined measure of collagen, such that the collagen is disposed within the incision at a place closer to the surface of the skin that is the medicinal and/or pharmaceutical substance.

2. A method of minimizing scarring and infection in the subcutaneous implantation of at least one collagen pellet having a medicinal and pharmaceutical substance into a living being, the method comprising the steps of:

1) Creating an incision subcutaneously into the body of the living being;

2) Inserting into the incision at least one predetermined measure of collagen; and 3) Then subsequently inserting into the incision at least one substance that is medicinal and/or pharmaceutical for the living being, such that the medicinal and/or pharmaceutical substance is disposed within the incision at a place closer to the surface of the skin that is the measure of collagen.

\* \* \* \* \*